(12) United States Patent
Mallinger et al.

(10) Patent No.: US 12,358,368 B2
(45) Date of Patent: *Jul. 15, 2025

(54) METHOD AND SYSTEM OF DEPLOYING SUBSTANCE DETECTION DEVICE FUNCTIONALITY

(71) Applicant: Consumer Safety Technology, LLC, Des Moines, IA (US)

(72) Inventors: Amanda Renee Mallinger, Des Moines, IA (US); Jennifer Ringgenberg, West Des Moines, IA (US); Usha Rani Chintala, Grimes, IA (US); Douglas Robert Bruce, Urbandale, IA (US); Sujitha Chandra Mohan, Waukee, IA (US)

(73) Assignee: Consumer Safety Technology, LLC, Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/760,886

(22) Filed: Jul. 1, 2024

(65) Prior Publication Data
US 2025/0001859 A1 Jan. 2, 2025

Related U.S. Application Data

(63) Continuation of application No. 17/889,808, filed on Aug. 17, 2022, now Pat. No. 12,030,380, which is a
(Continued)

(51) Int. Cl.
*B60K 28/06* (2006.01)
*G01N 33/497* (2006.01)
*A61B 5/00* (2006.01)

(52) U.S. Cl.
CPC ....... *B60K 28/063* (2013.01); *G01N 33/4972* (2013.01); *A61B 5/6893* (2013.01)

(58) Field of Classification Search
CPC .. B60K 28/063; G01N 33/4972; A61B 5/082; A61B 5/6893
See application file for complete search history.

(56) References Cited

U.S. PATENT DOCUMENTS

| 4,459,994 A | 7/1984 | Slemeyer |
| 4,749,553 A | 6/1988 | Phillips et al. |
| (Continued) | | |

FOREIGN PATENT DOCUMENTS

| CN | 204037354 | 12/2014 |
| CN | 104634951 | 5/2015 |
| (Continued) | | |

OTHER PUBLICATIONS

"Breath Alcohol Sensors," Datasheet for Dart Sensors Revised Sep. 20, 2016 (8 pages).
(Continued)

*Primary Examiner* — Karen Beck
(74) *Attorney, Agent, or Firm* — Pauly, DeVries Smith & Deffner LLC (57) ABSTRACT

A method and a system of deploying an ignition interlock device (IID). The method comprises receiving a time series of breath alcohol content (BrAC) measurements that are unitarily sourced from a pre-identified user, each BrAC measurement of the time series including an alveolar breath component and an interferent breath component; estimating a dissipation rate of alcohol attributable to the pre-identified user in accordance with the time series of BrAC measurements; determining, responsive to estimating the dissipation rate of alcohol, at least a subset of the BrAC measurements as being based on the alveolar breath component but not the interferent breath component; and performing one of triggering and not triggering the IID into a lockout state based on the at least a subset of the BrAC measurements.

20 Claims, 4 Drawing Sheets

Related U.S. Application Data continuation of application No. 16/940,101, filed on Jul. 27, 2020, now Pat. No. 11,427,083.

(56) References Cited

U.S. PATENT DOCUMENTS

| | | | |
|---|---|---|---|
| 4,926,164 A | 5/1990 | Breakspere et al. |
| 5,048,321 A | 9/1991 | Chow |
| 5,426,415 A | 6/1995 | Prachar et al. |
| 5,612,896 A | 3/1997 | Stock |
| 6,596,153 B1 | 7/2003 | Traylor |
| 6,795,775 B2 | 9/2004 | Traylor |
| 6,853,956 B2 | 2/2005 | Ballard et al. |
| 7,287,617 B2 | 10/2007 | Mobley et al. |
| 7,299,890 B2 | 11/2007 | Mobley et al. |
| 7,377,352 B2 | 5/2008 | Mobley et al. |
| 7,481,292 B2 | 1/2009 | Mobley et al. |
| 7,934,577 B2 | 5/2011 | Devries et al. |
| 7,992,422 B2 | 8/2011 | Leddy et al. |
| 8,174,394 B2 | 5/2012 | Ridder et al. |
| 8,179,271 B2 | 5/2012 | Kamiki |
| 8,256,286 B2 | 9/2012 | Carroll et al. |
| 8,370,027 B2 | 2/2013 | Pettersson et al. |
| 8,515,506 B2 | 8/2013 | Ridder et al. |
| 8,581,697 B2 | 11/2013 | Ridder et al. |
| 8,981,942 B2 | 3/2015 | He et al. |
| 9,290,174 B1 | 3/2016 | Zagorski et al. |
| 9,324,224 B2 | 4/2016 | Schumacher |
| 9,326,713 B2 | 5/2016 | Bellehumeur et al. |
| 9,442,103 B1 | 9/2016 | Goad |
| 9,901,288 B2 | 2/2018 | Gollar |
| 9,970,950 B1 | 5/2018 | Lynn et al. |
| 10,408,850 B1 | 9/2019 | Gordon et al. |
| 10,604,011 B2 | 3/2020 | Devries et al. |
| 10,663,440 B2 | 5/2020 | DeVries |
| 10,877,008 B2 | 12/2020 | Devries et al. |
| 10,877,023 B2 | 12/2020 | Ruland et al. |
| 11,427,083 B2 | 8/2022 | Mallinger et al. |
| 12,030,380 B2 | 7/2024 | Mallinger et al. |
| 2003/0109795 A1 | 6/2003 | Webber |
| 2004/0239510 A1 | 12/2004 | Karsten et al. |
| 2005/0087382 A1 | 4/2005 | Bellehumeur |
| 2005/0251060 A1 | 11/2005 | Gollar |
| 2006/0062255 A1 | 3/2006 | Holloway et al. |
| 2006/0130557 A1 | 6/2006 | Leddy et al. |
| 2006/0237253 A1 | 10/2006 | Mobley et al. |
| 2006/0237254 A1 | 10/2006 | Mobley et al. |
| 2006/0239856 A1 | 10/2006 | Mobley et al. |
| 2007/0062255 A1 | 3/2007 | Talton |
| 2007/0144812 A1 | 6/2007 | Stewart et al. |
| 2008/0061238 A1 | 3/2008 | Hok et al. |
| 2008/0117405 A1 | 5/2008 | Ridder et al. |
| 2008/0120052 A1 | 5/2008 | Ridder et al. |
| 2008/0316037 A1 | 12/2008 | Shoji et al. |
| 2009/0087920 A1 | 4/2009 | Pettersson et al. |
| 2009/0278698 A1 | 11/2009 | Kamiki |
| 2010/0063409 A1 | 3/2010 | Hoek |
| 2010/0268425 A1 | 10/2010 | Pettersson et al. |
| 2011/0009765 A1 | 1/2011 | Gollar |
| 2011/0178420 A1 | 7/2011 | Ridder et al. |
| 2011/0282167 A1 | 11/2011 | Ridder et al. |
| 2012/0078473 A1 | 3/2012 | Ridder et al. |
| 2012/0174651 A1 | 7/2012 | Mitchell |
| 2012/0197096 A1 | 8/2012 | Ridder et al. |
| 2013/0017276 A1 | 1/2013 | Blackman |
| 2013/0110311 A1 | 5/2013 | Ver et al. |
| 2013/0231871 A1 | 9/2013 | Hok et al. |
| 2013/0317328 A1 | 11/2013 | Ridder et al. |
| 2014/0061043 A1 | 3/2014 | Stock et al. |
| 2014/0155760 A1 | 6/2014 | Ridder et al. |
| 2014/0171759 A1 | 6/2014 | White et al. |
| 2014/0180500 A1 | 6/2014 | Hannon et al. |
| 2014/0377877 A1 | 12/2014 | Burgi et al. |
| 2015/0051807 A1 | 2/2015 | Desai et al. |
| 2015/0212063 A1 | 7/2015 | Wojcik et al. |
| 2015/0219620 A1 | 8/2015 | Hok et al. |
| 2015/0233897 A1 | 8/2015 | Hok et al. |
| 2015/0244452 A1 | 8/2015 | Wojciech et al. |
| 2015/0251660 A1 | 9/2015 | Nelson |
| 2015/0363582 A1 | 12/2015 | Sheller et al. |
| 2016/0054297 A1 | 2/2016 | Barbetta et al. |
| 2016/0146780 A1 | 5/2016 | Granstam et al. |
| 2016/0356764 A1 | 12/2016 | Martin et al. |
| 2016/0363582 A1 | 12/2016 | Blackley |
| 2017/0101006 A1 | 4/2017 | Devries et al. |
| 2017/0101007 A1 | 4/2017 | Devries et al. |
| 2017/0184537 A1 | 6/2017 | Umasankar et al. |
| 2018/0266985 A1 | 9/2018 | Farhad |
| 2019/0113502 A1 | 4/2019 | Ruland et al. |
| 2021/0148892 A1 | 5/2021 | Ruland et al. |
| 2022/0024308 A1 | 1/2022 | Mallinger et al. |
| 2023/0089401 A1 | 3/2023 | Mallinger et al. |

FOREIGN PATENT DOCUMENTS

| | | |
|---|---|---|
| DE | 3119341 | 12/1982 |
| EP | 0310672 | 4/1989 |
| EP | 1874578 | 7/2010 |
| EP | 2212147 | 8/2010 |
| EP | 2389100 | 5/2013 |
| EP | 2486403 | 6/2013 |
| EP | 2822797 | 1/2018 |
| GB | 2442980 | 4/2008 |
| GB | 2468522 | 8/2013 |
| JP | 0650918 | 2/1994 |
| JP | 2008232710 | 10/2008 |
| JP | 5154112 | 12/2012 |
| WO | 2006130129 | 12/2006 |
| WO | 2007094712 | 8/2007 |
| WO | 2010085716 | 7/2010 |
| WO | 2014031071 | 2/2014 |
| WO | 2014031072 | 2/2014 |
| WO | 2015181835 | 12/2015 |
| WO | 2016113353 | 7/2016 |

OTHER PUBLICATIONS

"Fuel Cell Sensors," Product Descriptions for Quad Cell and Standard Cell Sensors Retrieved from http://www.fuelcell-sensors.com Feb. 14, 2017 (14 pages).

"Intoxilyzer 8000 Operators Guide," https://romanolawpc.com/wp-content/uploads/2016/11/romano-law-oregon-intoxilyzer-8000-operators-guide-2006-09-08.pdf (Year: 2006), 57 pages.

"Non-Final Office Action," for U.S. Appl. No. 16/940,101 mailed Oct. 22, 2021 (8 pages).

"Non-Final Office Action," for U.S. Appl. No. 17/889,808 mailed Dec. 1, 2023 (5 pages).

"Notice of Allowance," for U.S. Appl. No. 16/940,101 mailed Mar. 21, 2022 (13 pages).

"Notice of Allowance," for U.S. Appl. No. 17/889,808 mailed Mar. 6, 2024 (13 pages).

"Operating Principle," for Figaro Sensors retrieved from http://www.figarosensor.com/technicalinfo/principle/mos-type.html on Feb. 14, 2017 (5 pages).

"Product Descriptions," for Alcohol and Carbon Monoxide Sensors produced by Dart Sensors retrieved from www.dart-sensors.com on Feb. 14, 2017 (5 pages).

"Response to Non Final Office Action," for U.S. Appl. No. 16/940,101, filed on Feb. 22, 2022 (11 pages).

"Understanding Breathalyzer Sensor Types," https://www.bactrack.com/blogs/expert-center/35043845 (year: 2015), 3 pages.

METHOD AND SYSTEM OF DEPLOYING SUBSTANCE DETECTION DEVICE FUNCTIONALITY

RELATED APPLICATIONS

This application is a continuation of U.S. Ser. No. 16/940,101, filed Jul. 27, 2020, which is a continuation of U.S. Ser. No. 17/889,808, filed Aug. 17, 2022, the contents of which are herein incorporated by reference.

TECHNICAL FIELD

The disclosure herein relates to vehicle ignition interlock devices deployed in breath alcohol monitoring and interfaces associated therewith.

BACKGROUND

Vehicles can incorporate breath alcohol ignition interlock devices (IID) to prevent a driver from operating a vehicle while intoxicated with alcohol. Such devices are designed to prevent a driver from starting a motor vehicle when the driver's breath alcohol content (BrAC) is at or above a mandated alcohol concentration threshold. Each state in the U.S. has adopted a law providing for use of such IID devices as a sanction for drivers convicted of driving while intoxicated, or as a condition of restoring some driving privileges after such offenses.

In operation, a driver uses an IID device by blowing into a mouthpiece portion of the IID coupled to an alcohol-sensing element such as a fuel cell that measures alcohol content of the driver's breath, to provide an objective representation or estimate of the blood alcohol concentration of the driver's bloodstream. The IID reads a signal generated from the fuel cell, or similar alcohol-sensing element, and determines whether the operator's breath alcohol content exceeds a threshold amount. If the operator's breath alcohol content does not exceed the threshold, the operator is determined as not intoxicated, and the IID enables the vehicle for operation by electrically enabling a system within the vehicle, such as a starter, fuel pump, or ignition system. If the breath sample delivered from the driver to IID registers a higher breath alcohol content than the predetermined allowable threshold, the vehicle is disabled from starting, and the IID device records a violation, which is also referred to as a failed sample.

DETAILED DESCRIPTION

Among other benefits and technical effects, embodiments provided herein provide ignition interlock functionality by way of triggering an IID to enact a vehicle operation lockout state in accordance with alveolar breath components but not interferent breath components from a series of breath alcohol content (BrAC) measurements of a vehicle operator.

A typical IID device meets guidelines established by the National Highway Traffic Safety Administration (NHTSA) in published model specifications for IIDs, which specify various tests that such a device must pass to make it an effective and reliable deterrent to intoxicated driving. For example, the model specifies tests designed to ensure a specified minimum volume of breath is delivered at a specified minimum flow rate against less than a specified maximum back pressure to ensure that an accurate result is produced, and specifies how such a device should be installed into a vehicle to prevent the vehicle from operating pending a determination that the driver is not intoxicated. The model specifications can also require that an installed IID pass a re-calibration test within a specified tolerance for at least seven days past its mandated recalibration period, which can vary from 30 to 90 days.

Embodiments herein recognize that legislation as enacted in most, if not all, jurisdictions are directed to preventing operation of a vehicle when the vehicle operator's blood alcohol content exceeds mandated amounts, where breath alcohol content as measured via an IID is used as a proxy for, or a representative by correlation with, blood alcohol content of the vehicle operator. Embodiments herein further recognize that presence of environmental, ambient, or other attendant non-ingested alcohol-containing substances may sufficiently influence breath alcohol measurements, causing an increased risk of false positive results in determining operator violations. Embodiments further recognize that any alcohol content in alveolar air, or deep lung air, is caused by ingested alcohol, or drinking events. Embodiments further recognize that alveolar, or deep lung, breath alcohol content determines operator bloodstream alcohol content to a much more significant degree than non-ingested alcohol contained in ambient sources. Furthermore, embodiments recognize that operator alcohol dissipation, or decay, rates of alcohol content are different for alveolar air breath samples indicative of metabolized alcohol, versus interferent-based breath samples.

The term interferent breath component as used herein indicates a breath sample alcohol content resulting from a non-ingested alcohol event. The non-ingested alcohol event, in some variations, is associated with non-ingested substances containing at least some alcohol content, such as mouthwash liquid, hand sanitizer fluid, or ambient vapor. To the extent that non-ingested alcohol-containing substances do not contribute to or affect blood alcohol content of a user of the IID, a breath alcohol detector may falsely indicate a higher level of alcohol intoxication than is actually the case, resulting in a false positive violation being generated.

As used herein, the term alveolar breath component refers to a breath alcohol content resulting from an alcohol consumption and ingestion event that directly contributes to an operator blood alcohol content via metabolism in conjunction with the human bloodstream. Alveolar air, or deep lung air, is generally presumed to be the primary component of a breath sample provided for measurement via the IID.

The likelihood of a discrete BrAC sample being due to an alcohol consumption or ingestion event can be identified over time by looking for a pattern among a series of discrete samples. Calculating the dissipation rate across several samples and correlating it with the rate of alcohol metabolism in humans can provide context for the individual samples, allowing for the individual samples to be designated on a violation continuum from highly unlikely to very likely to be based on actual alcohol consumption (wine, beer, liquor, for example).

Provided is a method of deploying ignition interlock device functionality. The method, executed in a processor of a mobile computing and communication device in one embodiment, comprises receiving a time series of breath alcohol content (BrAC) measurements that are unitarily sourced from a pre-identified user, each BrAC measurement of the time series including an alveolar, or deep lung, breath component and an interferent breath component; estimating a dissipation rate of alcohol attributable to the pre-identified user in accordance with the time series of BrAC measurements; determining, responsive to estimating the dissipation rate of alcohol, at least a subset of the BrAC measurements as attributable to the alveolar breath component but not the interferent breath component; and performing one of triggering and not triggering the IID into a lockout state based on the at least a subset of the BrAC measurements. A time series of breath alcohol content (BrAC) measurements is created by computing and storing the BrAC value of a user's breath each time the user provides a breath sample to the IID. Each time a user successfully provides a breath sample to the IID, a new entry to the time series is created. The IID computes the BrAC for the given sample and stores the computed BrAC as an entry in the time series. In an embodiment, the BrAC computed for the earliest acquired breath sample will be the first entry in the time series, the BrAC computed for the second acquired breath sample acquired at a the second earliest time will be the second entry in the time series, and so on. The BrAC computed for the nth acquired breath sample acquired at the nth time will be the nth entry in the time series, etc.

Also provided is a computing system for deploying an ignition interlock device (IID). The computing system, in embodiments, includes a processor and a non-transitory memory storing executable instructions. The instructions, when executed in the processor causing operations including receiving a time series of breath alcohol content (BrAC) measurements that are unitarily sourced from a pre-identified user, each BrAC measurement of the time series including an alveolar breath component and an interferent breath component; estimating a dissipation rate of alcohol attributable to the pre-identified user in accordance with the time series of BrAC measurements; determining, responsive to estimating the dissipation rate of alcohol, at least a subset of the BrAC measurements as attributable to the alveolar breath component but not the interferent breath component; and performing one of triggering and not triggering the IID into a lockout state based on the at least a subset of the BrAC measurements.

Further provided is a non-transitory memory medium storing executable instructions. The instructions, when executed in one or more processors, causing operations including accessing and displaying a time series of breath alcohol content (BrAC) measurements that are unitarily sourced from a pre-identified user, each BrAC measurement of the time series including an alveolar breath component and an interferent breath component; estimating a dissipation rate of alcohol attributable to the pre-identified user in accordance with the time series of BrAC measurements; determining, responsive to estimating the dissipation rate of alcohol, at least a subset of the BrAC measurements as attributable to the alveolar breath component but not the interferent breath component; and performing an evaluation as to whether the IID being triggered, or not triggered, into a lockout state based on the at least a subset of the BrAC measurements constitutes a violation in accordance with a predetermined breath alcohol threshold content.

One or more embodiments described herein can be implemented using programmatic modules, engines, or components. Furthermore, one or more embodiments described herein may be implemented through the use of instructions that are executable by one or more processors. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines.

Some embodiments described herein can generally require the use of computing devices, including processor and memory resources. For example, one or more embodiments described herein may be implemented, in whole or in part, on computing devices such as servers, desktop computers, mobile devices including cellular or smartphones, wearable devices, tablet devices and laptop computing devices. Memory, processing, and network resources may all be used in connection with the establishment, use, or performance of any embodiment described herein, including with the performance of any method or with the implementation of any system.

One or more embodiments described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device. A programmatically performed step may or may not be automatic.

Figure 1:
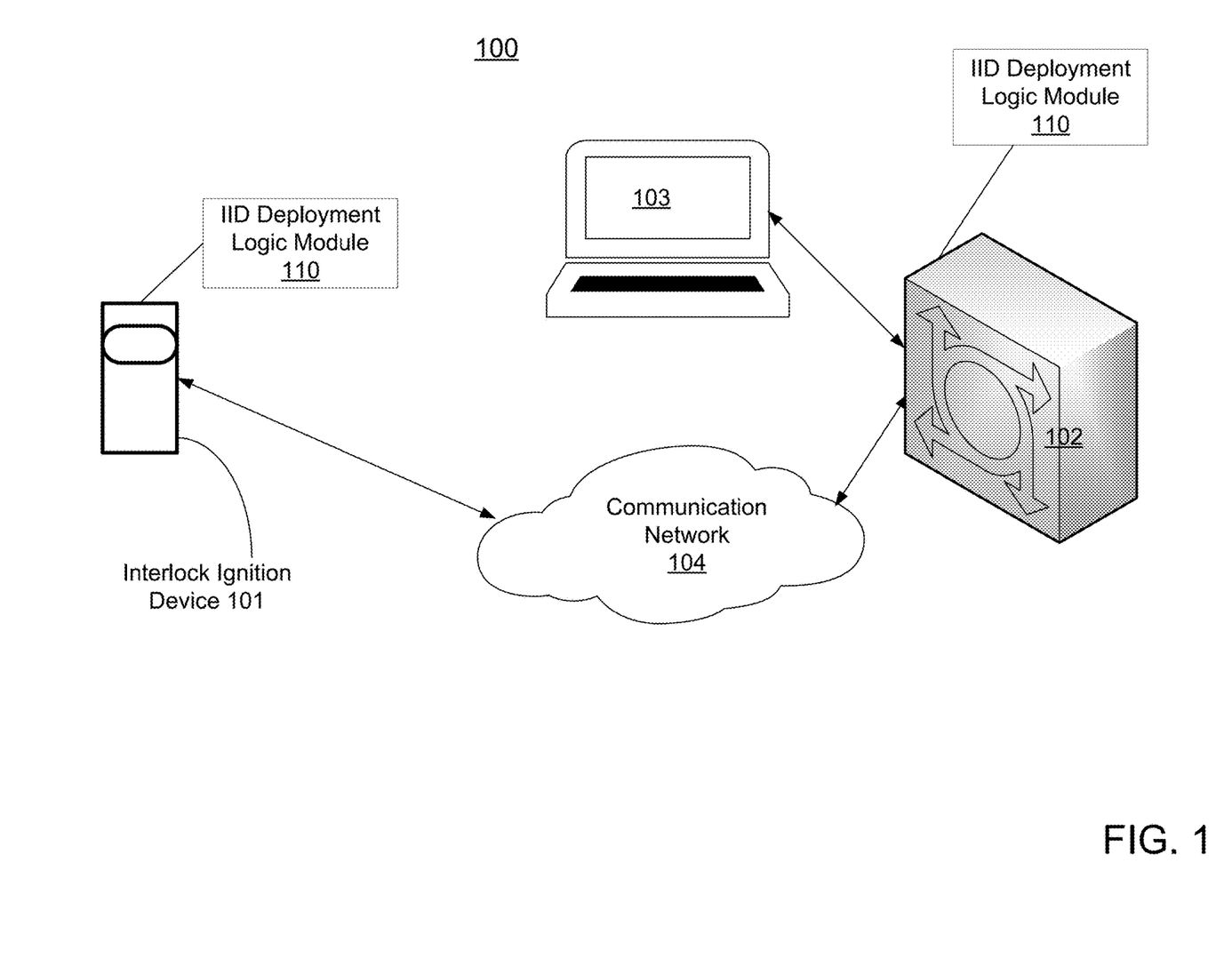
FIG. 1 illustrates a computing and communication system for deploying an ignition interlock device (IID) in accordance with embodiments herein.

FIG. 1 illustrates a computing and communication system 100 in deploying ignition interlock device (IID) 101 in accordance with embodiments herein. IID 101 includes a processor and a memory. The memory stores executable instructions, constituting IID deployment logic module 110, for triggering IID 101 into enacting a vehicle lockout state based on a set or subset of BrAC measurements in accordance with an alveolar breath component but not an interferent breath component. In variations, some portions, or all, of the executable instructions constituting IID deployment logic module 110 may be hosted at server device 102, or laptop or desktop computer 103 that are in communication with IID 101 via communication network 104. In this scenario, there may not be an IID deployment logic module 110 located at the IID 101. If a user, or vehicle operator provides a sample at IID 101 that exceeds the mandated breath alcohol limit, then IID 101 will trigger a lockout, or disabled, state of the vehicle in which the IID is deployed.

Figure 2:
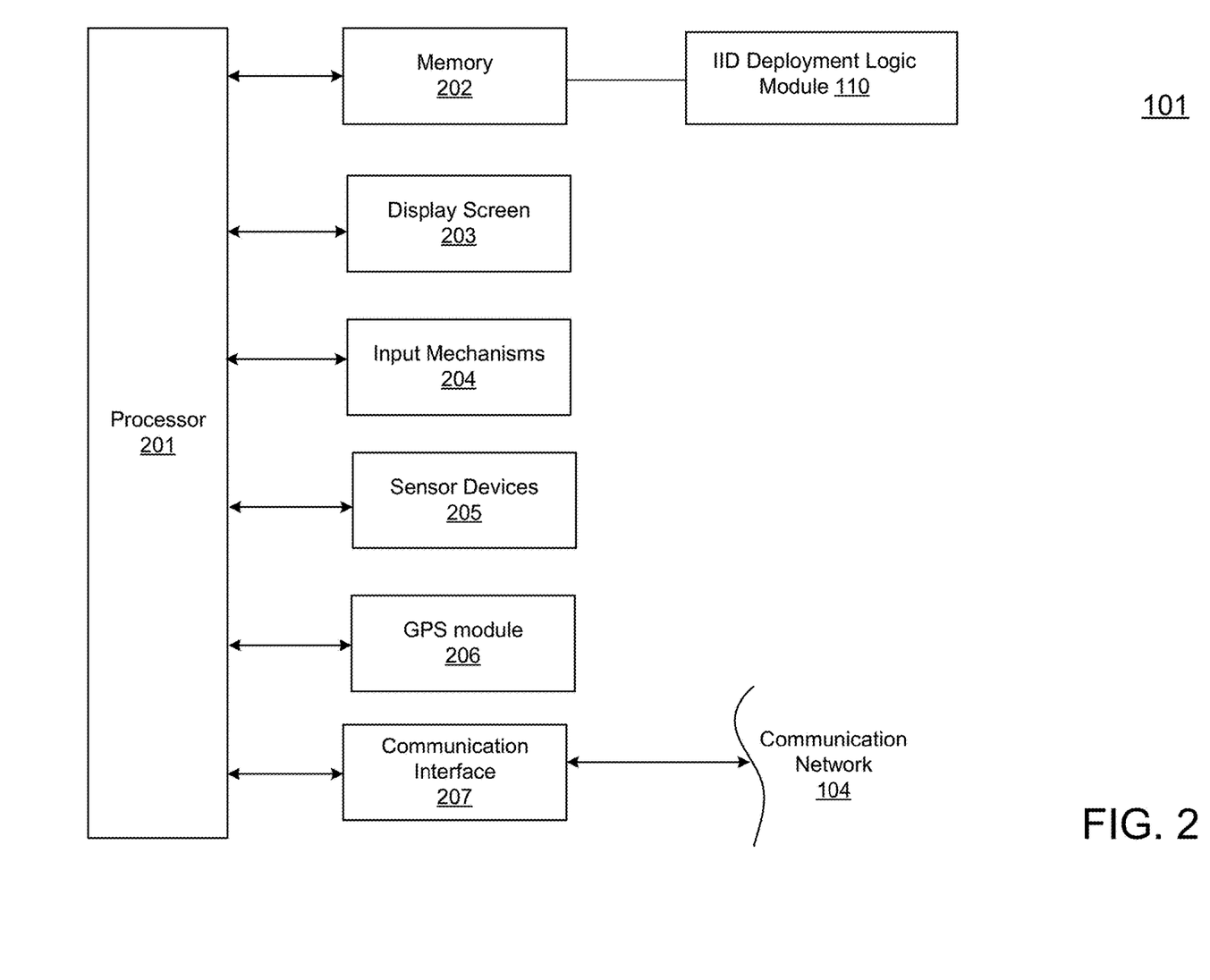
FIG. 2 illustrates an example architecture of a computing and communication device for deploying ignition interlock device functionality.

FIG. 2 illustrates an example architecture of a breath alcohol ignition interlock device 101 for deploying ignition interlock device functionality at least in part based on IID deployment logic module 110. In one embodiment, ignition interlock device 101 may include or be interconnected with, for example, one or more of cellular or other wireless computing and communication capable of telephony, messaging, and data computing services. Ignition interlock device may include processor 201, memory 202, display screen 203, input mechanisms 204 such as resistive- or capacitance-based input mechanisms or software-implemented touchscreen input functionality, sensor devices 205, and GPS module 206. IID 101 may also include capability for detecting and communicatively accessing wireless communication signals, including but not limited to any of Bluetooth, Wi-Fi, RFID, and GPS signals, and incorporate communication interface 207 for communicatively coupling to communication network 104, such as by sending and receiving cellular data over data channels and voice channels.

IID deployment logic module 110, in one embodiment can be embodied in a downloaded mobile application stored in memory 202 of IID 101 may include processor-executable instructions stored in RAM, for deploying functionality of IID 101.

IID deployment logic module 110 includes instructions executable in processor 201 to receive a time series of breath alcohol content (BrAC) measurements that are unitarily sourced from a pre-identified user, each BrAC measurement of the time series including an alveolar, or deep lung, breath component and an interferent breath component.

IID deployment logic module 110 also includes instructions executable in processor 210 to estimate a dissipation rate of alcohol attributable to the pre-identified user in accordance with the time series of BrAC measurements.

IID deployment logic module 110 further includes instructions executable in processor 210 to determine, responsive to estimating the dissipation rate of alcohol, a subset of the BrAC measurements as attributable to an alveolar breath component but not an interferent breath component.

In some variations, the alcohol dissipation rate attributable to the interferent breath component exceeds 0.025 g/100 ml/hour, whereas the alcohol dissipation rate attributable to the alveolar breath component ranges from 0.015 to 0.025 g/100 mL/hour.

IID deployment logic module 110 also includes instructions executable in processor 210 to either trigger, or not trigger, the IID into a lockout state based on the at least a subset of the BrAC measurements.

In some embodiments, an alcohol dissipation rate of the interferent breath component of the BrAC measurements exceeds an alcohol dissipation rate attributable to the alveolar breath component.

In some embodiments, the alveolar breath component is indicative of an alcohol ingestion event.

In additional aspects, the interferent breath component is indicative of a non-ingested alcohol event. The non-ingested alcohol event, in some variations, is associated with non-ingested substances containing at least some alcohol content, for instance, deriving from a mouthwash liquid, a hand sanitizer fluid, or an ambient vapor.

In some embodiments, the IID is triggered into the lockout state when the alveolar breath component of the at least a subset of the breath alcohol measurements indicates that a predetermined threshold of blood alcohol content is exceeded.

In yet other aspects, the IID is not triggered into the lockout state when the alveolar breath component of the at least a subset of the breath alcohol measurements indicates that a predetermined threshold of blood alcohol content is not exceeded.

In some embodiments, the time series of BrAC measurements comprises a series of breath sample BrAC measurements acquired from the pre-identified user at measured time intervals.

In some variations, the measured time intervals can be either a regular duration or an irregular duration between at least a trio of successive BrAC measurements within the time series of breath sample BrAC measurements. In some variations, the time series of BrAC measurements can include three, four, five, six, seven, eight, or more measurements. In some variations, the time intervals between the BrAC measurements are at least about or are about thirty seconds, one minute, two minutes, three minutes, four minutes, or five minutes. In some variations, the time intervals between the BrAC measurements are at most about two minutes, three minutes, four minutes, five minutes, seven minutes, eight minutes, nine minutes, 10 minutes, 15 minutes, 20 minutes, or 30 minutes.

Figure 3:
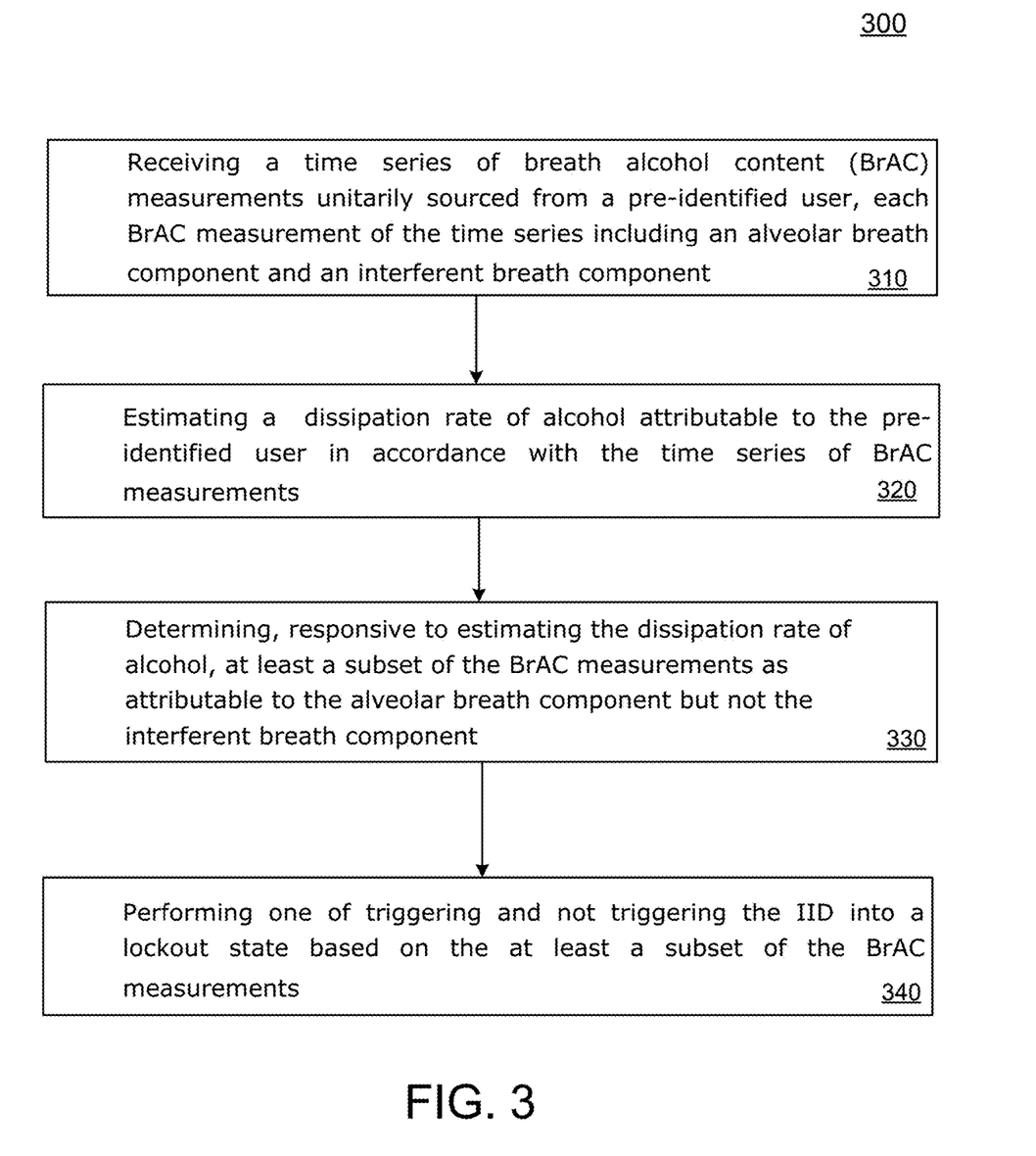
FIG. 3 illustrates, in an example embodiment, a method of deploying ignition interlock device functionality.

FIG. 3 illustrates, in an example embodiment, a method 300 of deploying ignition interlock device functionality.

Examples of method steps described herein are related to the use of IID 101 used in deploying IID functionality. According to one embodiment, the techniques are performed by the processor 201 executing one or more sequences of software logic instructions that constitute IID deployment logic module 110 of IID 101. In embodiments, IID deployment logic module 110 may be hosted at server device 102 and is communicative with IID 101 and portable or desktop computer 103, and includes sequences of processor-executable instructions. Such instructions may be read into memory 202 from machine-readable medium, such as memory storage devices. Executing the instructions of IID deployment logic module 110 stored in memory 202 causes processor 201 to perform the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, receiving a time series of breath alcohol content (BrAC) measurements that are unitarily sourced from a pre-identified user, each BrAC measurement of the time series including an alveolar (deep lung) breath component and an interferent breath component.

At step 320, estimating a dissipation rate of alcohol attributable to the pre-identified user in accordance with the time series of BrAC measurements.

At step 330, determining, responsive to estimating the dissipation rate of alcohol, at least a subset of the BrAC measurements as attributable to the alveolar breath component but not the interferent breath component.

At step 340, performing one of triggering and not triggering the IID into a lockout state based on the at least a subset of the BrAC measurements In some embodiments, an alcohol dissipation rate of the interferent breath component of the BrAC measurements exceeds an alcohol dissipation rate attributable to the alveolar breath component.

Figure 4:
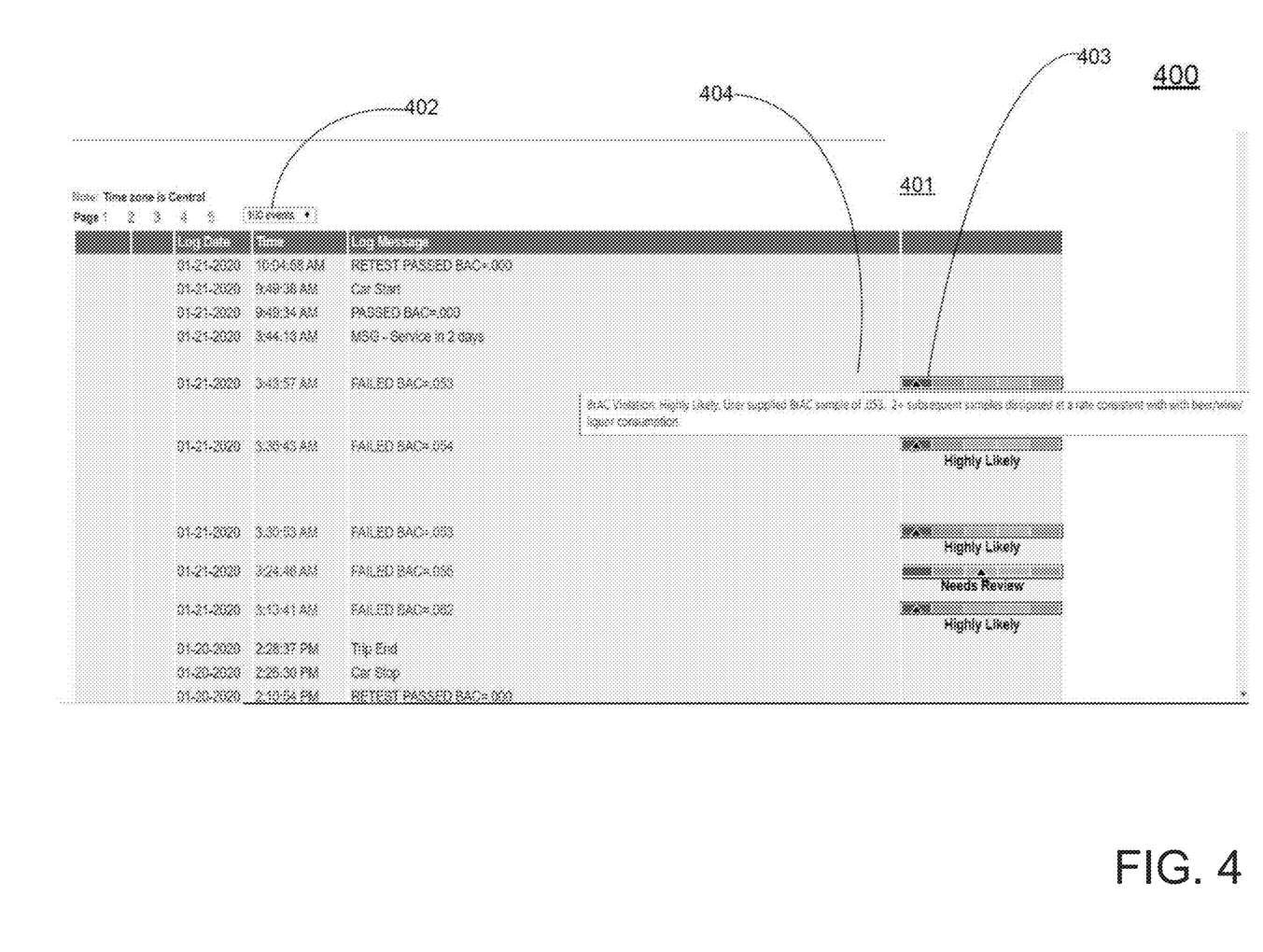
FIG. 4 illustrates, in an example embodiment, a user interface display deployment of ignition interlock device functionality.

FIG. 4 illustrates, in example embodiment 400, a user interface display deployment of ignition interlock device functionality. In embodiments, a non-transitory memory medium stores executable instructions, which, when executed in one or more processors, cause operations including accessing, from the memory, and displaying at display interface 401 a time series 402 of breath alcohol content (BrAC) measurements that are acquired from a single pre-identified user, each BrAC measurement of the time series including an alveolar breath component and an interferent breath component; estimating a dissipation rate of alcohol attributable to the pre-identified user in accordance with the time series of BrAC measurements; determining, responsive to estimating the dissipation rate of alcohol, at least a subset of the BrAC measurements as attributable to the alveolar breath component but not the interferent breath component; and performing an evaluation as to whether the IID being triggered, or not triggered, into a lockout state based on the at least a subset of the BrAC measurements constitutes a violation, or not a violation, in accordance with a predetermined breath alcohol threshold content.

Because interferents or contaminants can affect breathalyzers, the ability for a system to identify a likelihood that a given reading is due to a contaminant rather than an alcohol consumption event is advantageous. Monitoring authorities can use this method to quickly scan and identify likely noncompliant drivers versus those who simply tried to start their car too soon after rinsing their mouth with mouthwash or recently eating something containing a high concentration of yeast, for example.

In illustrative embodiments of display interface 401, visual likelihood indicator scale 403 displays one of five likelihood indicators that the breath alcohol content as measured at the IID constitutes a violation. The visual likelihood indicator scale 403 is shown underneath the heading "Intoxavisor™ Beta" in FIG. 4. In one embodiment, by hovering a display screen cursor over a resultant likelihood indicator scale 403, message 404 is invoked and rendered, providing additional detail of alcohol dissipation rates associated with one or more particular violations flagged within the time series of breath sample measurements. When a flagged BrAC appears within the data log, likelihood indicator scale 403 also appears with "Highly Likely", "Somewhat Likely", "Needs Review", "Somewhat Unlikely", "Highly Unlikely" indicated visually. In some examples, the likelihood indicator scale 403 provides one of five recommendations or likelihood indicators regarding whether a particular violation or failed breath test is a result of alveolar breath or interferent breach. It is also possible for the likelihood indicator scale 403 to provide one of a different number of likelihood indicators, such as two, three, four, six, or seven. The likelihood indicator from the likelihood indicator scale 403 will depend on the rate of decay of a time series of breath alcohol measurement samples. In some examples, if the time series of measurements indicates a faster dissipation rate consistent with interferent alcohol, then the likelihood indicator may be "Needs Review", "Somewhat Unlikely", or "Highly Unlikely". In some examples, if the time series of measurements indicates a slower dissipation rate, consistent with alveolar alcohol, then the likelihood indicator may be "Highly Likely" or "Somewhat Likely", in some examples.

In one illustrative example embodiment, BrAC measurements before and after a given failed sample are used to analyze the likelihood that the given failed sample was due to or primarily due to an alveolar breath component of the breath sample. To analyze the given failed sample, three previous samples and five subsequent samples can be used, limited to a timeframe: 60 mins prior to violation till the time it takes for the alcohol to completely dissipate at the rate of 0.015 g/100 mL/hour.

A likely violation is determined if 3+ samples in excess of threshold content with dissipation rate<0.015 g/100 mL/hour exist and a sample with dissipation rate>0.025 g/100 mL/hour doesn't exist.

A result is determined as unlikely to be a violation if 1 failed sample in excess of threshold content with subsequent sample dissipation rate>0.025 g/100 mL/hour within a 20 minute window.

In some embodiments, if a sample determined as a violation does not meet the above conditions, it may be marked as indeterminate, or flagged for additional review.

In another illustrative example embodiment shown in FIG. 4, BrAC measurements before a given failed sample (four previous samples), are used to analyze the likelihood that the given failed sample was due to or primarily due to an alveolar breath component of the breath sample. In this example, the given failed sample was provided at 3:43:57 AM. Four previously provided samples are used to evaluate the dissipation rate, specifically, the samples provided at 3:36:43 AM, 3:30:53 AM, 3:24:46 AM, and 3:13:41 AM. Each of these previous samples is within 60 minutes of the given failed sample. Each of these samples also show a failed BAC measurement. In this example, the BrAC measurements at the four previous timepoints are 0.054, 0.053, 0.055, and 0.062, respectively. This indicates a slower dissipation rate of from 0.015 to 0.025 g/100 mL/hour. As a result, a conclusion is drawn that the alcohol present in the previous samples and the given sample dissipated at a rate consistent with alcohol consumption rather than with interferent alcohol. That conclusion is reflected in the likelihood indicator "Highly Likely" shown for the BrAC Measurement of 0.053 at 3:43:57 AM. This conclusion is also present in the message 404 stating, "BrAC Violation: Highly Likely. User supplied BrAC sample of 0.053. 2+ previous samples dissipated at a rate consistent with beer/wine/liquor consumption."

As used in the specification and appended claims herein, the singular forms "a," "an," and "the" encompass plural referents unless the content clearly dictates otherwise. It should also be noted that the term "or" is generally employed in its sense including "and/or" unless the content indicates otherwise. Furthermore, as used in the disclosure herein and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged.

It is contemplated for embodiments described herein to extend to individual elements and concepts described herein, independently of other concepts, ideas or system, as well as for embodiments to include combinations of elements recited anywhere in this application. Although embodiments are described in detail herein with reference to the accompanying drawings, it is contemplated that the disclosure herein is not limited to only such literal embodiments. As such, many modifications including variations in sequence of the method steps in conjunction with varying combinations of user interface features disclosed herein will be apparent to practitioners skilled in this art. Accordingly, it is intended that the scope of the invention be defined by the following claims and their equivalents. Furthermore, it is contemplated that a particular feature described either individually or as part of an embodiment can be combined with other individually described features, or parts of other embodiments. Thus, the absence of describing combinations, including user interface manifestations of such, do not preclude the inventor from claiming rights to such combinations.

The invention claimed is:

1. A method of deploying a substance detection device, the method comprising:
receiving an initial sample volume of breath from a user;
measuring a breath alcohol content (BrAC) of the initial sample volume of breath with an alcohol-sensing element of the substance detection device;
after measuring the BrAC of the initial sample volume of breath, receiving a subsequent sample volume of breath from the user;

measuring the BrAC of the subsequent sample volume of breath with the alcohol-sensing element of the substance detection device;

wherein the initial sample volume of breath and the subsequent sample volume of breath each comprise at least one of an alveolar breath component and an interferent breath component;

estimating a dissipation rate of alcohol between the initial sample volume of breath and the subsequent sample volume of breath; and determining, responsive to estimating the dissipation rate of alcohol, at least a subset of the BrAC measurements as attributable to the alveolar breath component but not the interferent breath component.

2. The method of claim 1, wherein an alcohol dissipation rate attributable to the interferent breath component of the BrAC measurements exceeds a dissipation rate attributable to the alveolar breath component.

3. The method of claim 2, wherein the alcohol dissipation rate attributable to the interferent breath component exceeds 0.025 g/100 mL/hour, and the dissipation rate attributable to the alveolar breath component ranges from 0.015 to 0.025 g/100 mL/hour.

4. The method of claim 1, wherein the alveolar breath component is indicative of an alcohol ingestion event.

5. The method of claim 1, wherein the interferent breath component is indicative of a non-ingested alcohol event.

6. The method of claim 1, further comprising performing one of triggering and not triggering the substance detection device into a violation state based on the at least a subset of the BrAC measurements.

7. The method of claim 6, further comprising triggering the substance detection device into the violation state when the alveolar breath component of the at least a subset of the BrAC measurements indicates that a predetermined threshold of blood alcohol content is exceeded.

8. The method of claim 6, further comprising not triggering the substance detection device into the violation state when the alveolar breath component of the at least a subset of the BrAC measurements indicates that a predetermined threshold of blood alcohol content is not exceeded.

9. The method of claim 1, wherein the BrAC measurements comprise a series of BrAC measurements acquired from the user at measured time intervals.

10. The method of claim 9, wherein the measured time intervals comprise one of a regular duration and a random duration between at least a trio of successive BrAC measurements within the time series of BrAC measurements.

11. A computing system for deploying a substance detection device, the computing system comprising:

a processor;

one or more memory resources storing a set of instructions, the instructions when executed in the processor causing operations comprising:

receiving a initial sample volume of breath from a user;

measuring a breath alcohol content (BrAC) of the initial sample volume of breath with an alcohol-sensing element of the substance detection device;

after measuring the BrAC of the initial sample volume of breath, receiving a subsequent sample volume of breath from the user;

measuring the BrAC of the subsequent sample volume of breath with the alcohol-sensing element of the substance detection device;

wherein the initial sample volume of breath and the subsequent sample volume of breath comprise an alveolar breath component and an interferent breath component;

estimating a dissipation rate of alcohol between the initial sample volume of breath and the subsequent sample volume of breath; and determining, responsive to estimating the dissipation rate of alcohol, at least a subset of the BrAC measurements as attributable to the alveolar breath component but not the interferent breath component.

12. The computing system of claim 11, wherein an alcohol dissipation rate attributable to the interferent breath component of the BrAC measurements exceeds a dissipation rate attributable to the alveolar breath component.

13. The computing system of claim 12, wherein the alcohol dissipation rate attributable to the interferent breath component exceeds 0.025 g/100 mL/hour, and the dissipation rate attributable to the alveolar breath component ranges from 0.015 to 0.025 g/100 mL/hour.

14. The computing system of claim 11, wherein the alveolar breath component is indicative of an alcohol ingestion event.

15. The computing system of claim 11, wherein the interferent breath component is indicative of a non-ingested alcohol event.

16. The method of claim 11, the operations further comprising performing one of triggering and not triggering the substance detection device into a violation state based on the at least a subset of the BrAC measurements.

17. The computing system of claim 16, further comprising instructions causing triggering the substance detection device into the violation state when the alveolar breath component of the at least a subset of the BrAC measurements indicates that a predetermined threshold of blood alcohol content is exceeded.

18. The computing system of claim 16, further comprising instructions causing not triggering the substance detection device into the violation state when the alveolar breath component of the at least a subset of the BrAC measurements indicates that a predetermined threshold of blood alcohol content is not exceeded.

19. The computing system of claim 11, wherein the BrAC measurements comprise a series of BrAC measurements acquired from the user at measured time intervals.

20. The method of claim 1, further comprising, generating at a display interface, one of a plurality likelihood indicators, wherein each likelihood indicator is indicative of whether the BrAC of the initial sample is a result of the alveolar breath component or the interferent breath component.

* * * * *